United States Patent [19]

Takaishi et al.

[11] 3,976,709

[45] Aug. 24, 1976

[54] PROCESS FOR THE PREPARATION OF TRICYCLO[5.3.1.0$^{3,8}$]UNDECANE

[75] Inventors: Naotake Takaishi; Yoshiaki Inamoto, both of Wakayama; Kiyoshi Tsuchihashi, Kainan, all of Japan

[73] Assignee: Kao Soap Co., Ltd., Tokyo, Japan

[22] Filed: May 30, 1975

[21] Appl. No.: 582,108

[30] Foreign Application Priority Data

June 4, 1974 Japan.................................. 49-63236

[52] U.S. Cl. ....................... 260/666 PY; 260/666 M
[51] Int. Cl.$^2$........................................... C07C 13/54
[58] Field of Search .................. 260/666 PY, 666 M

[56] References Cited
OTHER PUBLICATIONS

Kautz et al., Chem. Commun. 1971, 1287.
Kautz et al., J. Amer. Chem. Soc., 95.5662, 1973.
Schleyer et al., Chem. Letters, 1189, 1973.
N. S. Vorobeva, O. A. Arefev, V. I. Epshea, and A. A. Petrov, Chem. Ab. 75:19562e, (Nefteklimiya 11,163, 1970).
Naotake Takaishi et al., J. Org. Chem. 40, No. 3, pp. 276–281, 1975.

*Primary Examiner*—Veronica O'Keefe
*Attorney, Agent, or Firm*—Woodhams, Blanchard and Flynn

[57] ABSTRACT

A process for the preparation of tricyclo[5.3.1.0$^{3,8}$]-undecane in which 6,7-endo-trimethylenebicyclo[3.2.1]octane is isomerized in the presence of an acid catalyst.

5 Claims, No Drawings

PROCESS FOR THE PREPARATION OF TRICYCLO[5.3.1.0³,⁸]UNDECANE

BACKGROUND OF THE INVENTION

1. FIELD OF THE INVENTION

This invention relates to a process for the preparation of tricyclo[5.3.1.0³,⁸]undecane (II). More particularly, this invention relates to a process for preparing tricyclo[5.3.1.0³,⁸]undecane (II) (hereinafter referred to as "4-homoisotwistane") by isomerizing 6,7-endo-trimethylenebicyclo[3.2.1]octane (I) as shown by the following reaction scheme:

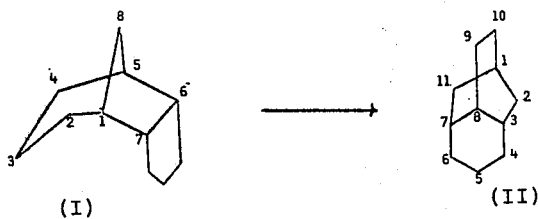

As is seen from the formula (II), 4-homoisotwistane (II) is a tricyclic saturated aliphatic hydrocarbon having cagelike molecular structure. It can be transformed to 1-methyladamantane, a known useful compound, as described in U.S. Ser. Nos. 485,068 and 485,069, both filed July 2, 1974 now U.S. Pat. Nos. 3,894,100 and 3,894,101. In view of its molecular structure, 4-homoisotwistane (II) will be useful as an antiviral agent, a modifier moiety for various pharmaceutical compounds, an additive for lubricating oils, a high-pressure lubricant, a rust-preventive agent, an oiling agent for fibers and the like, in the same manner as known adamantane compounds. See section entitled "Adamantane" in the Supplement Volume of Kirk-Othmer's "Encyclopedia of Chemical Technology".

2. DESCRIPTION OF THE PRIOR ART

Several processes for the synthesis of 4-homoisotwistane (II) are known in the art. For example, the synthesis of this compound is disclosed by Krantz et al, *Chem. Commun.*, 1287 (1971) and *J. Amer. Chem. Soc.*, 95, 5662 (1973), Majerski et al, *Tetrahedron Lett.*, 4915 (1973), and Schleyer et al, *Chemistry Lett.*, 1189 (1973).

We previously found that 4homoisotwistane (II) can be synthesized by isomerizing, in the presence of an acid catalyst, 5,6-exo-tetramethylenenorbornane (III) of the following formula:

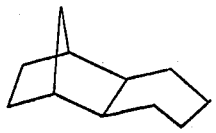

and 5,6-trimethylenebicyclo[2.2.2]octane (IV) of the following formula:

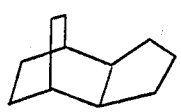

(see Chemistry Lett., 1185, (1973) and Japanese Patent Application No. 77621/73 (U.S. Ser. No. 485,068 now U.S. Pat. No. 3,894,100) and No. 77622/73 (U.S. Ser. No. 485,067)).

SUMMARY OF THE INVENTION

As a result of our further research, we discovered that 6,7-endo-trimethylenebicyclo[3.2.1]octane can be isomerized very promptly, in a good yield, to 4-homoisotwistane (II) under specific reaction conditions. Based on this finding, we have now completed this invention.

Nothing is known in the art about the isomerization of 6,7-endo-trimethylenebicyclo[3.2.1]octane (I) in the presence of an acid catalyst. N. S. vorobova, O. A. Arefev, V. I. Epshev and A. A. Petrov disclose that when 6,7-trimethylenebicyclo[3.2.1]octane is treated with an aluminum halide, 1- and 2-methyladamantanes can be obtained (Neftekhimiya, 11, 63 (1971)). However, they did not mention whether or not the 6,7-trimethylene group in their starting substance has an exo- or an endo-configuration. Further, they did not disclose whether or not 4-homoisotwistane (II) might be formed in the course of the reaction.

As a result of our research on the isomerization of 6,7-endo-trimethylenebicyclo[3.2.1]octane (I), in the presence of an acid catalyst, it was discovered that, although in this reaction there was finally obtained a thermodynamic equilibrium mixture of 1- and 2-methyladamantanes, partway through this reaction there were formed a number of reaction intermediates including 4-homoisotwistane (II). These intermediates are formed at various stages of the complicated reaction pathways starting from (I), which reaction pathways comprise a complex combination of competitive and consecutive reactions. When the reaction is stopped partway to completion there is obtained a mixture containing a variety of intermediates, the ratio of which is determined by the reaction conditions and the reaction time. We discovered that if the reaction conditions such as the types and amounts of the catalyst and solvent, as well as the reaction temperature and time, are appropriately chosen in the above reaction, there can be obtained a reaction product mixture in which the proportion of 4-homoisotwistane (II) in the reaction mixture is a maximum (more than 85 weight percent under favorable conditions).

We previously studied, also, the isomerization of 6,7-exo-trimethylenebicyclo[3.2.1]octane (V) of the following formula:

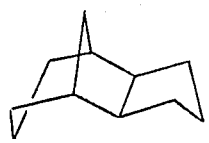

which is a configurational isomer of the starting substance (I) of this invention (J. Org. Chem., 40, 276 (1975)). A comparison of the isomerization rates of the endo-(I) and the exo-(V) isomers revealed that the endo-isomer (I) was $10^5$ times more faster reactive than the exo-isomer. Two advantages among many others, can be cited arising from the use of 6,7-endo-trimethylenebicyclo[3.2.1]octane (I) as the starting material of this invention. Firstly, since the rate of the isomerization reaction of (I) is very high, the intended product can be obtained even if the amount of the catalyst is reduced or there is used a catalyst having a low activity. Secondly, since the reaction time can be shortened and since it is possible to reduce the amount of the catalyst or to use a catalyst having a low activity, it is very easy to prevent the isomerization reaction from proceeding beyond the stage of 4-homoisotwistane (II), the desired product of this invention.

As is apparent from the foregoing, 6,7-endo-trimethylenebicyclo[3.2.1]octane (I) is very advantageous as the starting substance for the synthesis of 4-homoisotwistane (II). However, since the starting compound (I) can be finally converted to 1- and 2-methyladamantanes as described hereinabove, in order to recover 4-homoisotwistane (II), in high yield, it is necessary to perform the reaction under limited reaction conditions. The term "reaction under limited conditions" means a reaction in which isomerization is stopped at an appropriate time, a reaction in which the amount of the catalyst is reduced or in which a catalyst having a relatively low activity is used, a reaction in which isomerization is carried out in the presence of a solvent, a reaction in which isomerization is carried out at a relatively low temperature, and a reaction which is carried out using an appropriate combination of two or more of these reaction procedures. The isomerization reaction under limited conditions is carried out so that the isomerization reaction is stopped at a stage at which the content of [5.3.1.0$^{3,8}$]undecane (II) in the reaction mixture is at least about 60 weight percent, and is preferably at the highest level that can be attained under the reaction conditions which is usually up to about 80 weight percent.

In contrast, when the reaction is carried out under such drastic conditions as the use of strong Lewis acid catalysts such as aluminum halides and antimony pentahalides, in as large an amount as 50 mole percent or more, based on the starting substance (I), in the absence of solvent, at elevated temperature exceeding about 50°C., the starting substance is rapidly converted to the final methyladamantanes, and various intermediates including 4-homoisotwistane (II), which is the desired product of this invention, are hardly detected.

In order to establish the limited reaction conditions employed in the process of this invention, there can be employed as catalyst Brønsted acids such as sulfuric acid, fluorosulfonic acid, chlorosulfonic acid, alkanesulfonic acid, e.g., methanesulfonic acid, trifluoromethanesulfonic acid and ethanesulfonic acid, and arenesulfonic acids, e.g., benzenesulfonic acid, and p-toluenesulfonic acid. The amount of such Brønsted acid catalysts can be from 0.1 to 20 moles, preferably from 1 to 10 moles, per one mole of starting substance (I). Further, it is possible to use as catalyst Lewis acids such as aluminum halides, boron trifluorode and antimony pentahalides, in an amount of from 0.01 to 0.5 moles, per one mole of the starting substance (I).

In order to complete the reaction in a short time, Bronsted acid catalysts may be used in a molar equivalent amount or excess, but in order to avoid extensive reaction of the intermediate, Lewis acid catalysts should be used in amounts not exceeding 50 mole percent. These catalysts can be used in the form of mixtures of two or more of them. For instance, if a combination of sulfuric acid and boron trifluoride is used, a synergistic effect is observed.

In the process of this invention, favorable results are often obtained if a solvent is used, in addition to the above-mentioned appropriate selection of the kind and amount of the catalyst. One of the reasons therefor is that the starting substance (I) is solid at room temperature. The type of solvent used is not critical. Any solvents which are inert to the catalyst, such as aromatic hydrocarbons, aliphatic hydrocarbons, halogenated hydrocarbons and ethers, can be used. Further, these solvents can be used in combination with any of the foregoing catalysts (and mixtures thereof). Moreover, the amount of the solvent used is not critical. For example, the amount of the solvent can be from 0.1 to 500 times the weight of the starting material (I).

The isomerization reaction of the process of this invention proceeds at temperatures ranging from −30°C. to +100°C., but it is preferred to carry out the reaction at −10° to +50°C.

6,7-endo-trimethylenebicyclo[3.2.1]octane (I) used as the starting substance in this invention is a novel substance, the synthesis of which has not been reported. This novel compound can easily be synthesized by a combination of known reactions, for example, in the following reaction sequence (the present inventors, J. Org. Chem., 40,276 (1975). 5,6-endo-trimethylenenorbornene-2 (VI) formed by the Diels-Alder reaction between dicyclopentadiene and cyclopentene (Cristol et al, J. Am. Chem. Soc., 82, 2351 (1960)) is subjected to ring expansion with dichlorocarbene (Jefford et al, Org. Syntheses, 51, 60 (1971)). The resulting product (VII) is then dehalogenated and then is hydrogenated to the desired compound (I). This reaction course is represented by the following reaction scheme:

(VI)

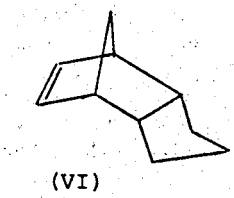

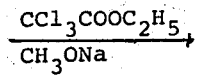

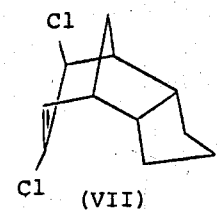

(VII)

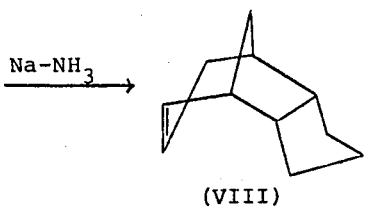

(VIII)

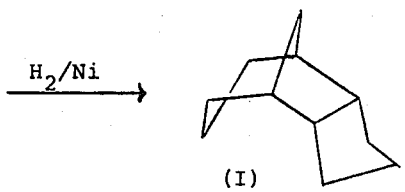

(I)

The invention will now be further described in detail by reference to the following illustrative Examples. Since the starting compound, 6,7-endo-trimethylenebicyclo[3.2.1]octane (I), is a novel compound, the synthesis of this compound is also described in detail by reference to the following Preparation.

Preparation (a) Synthesis of 3,4-dichloro-6,7-endo-trimethylenebicyclo[3.2.1]oct-2-ene (VII):

A four-neck round-bottom flask having a capacity of 1 liter was charged with 33.5 g (0.25 mole) of 5,6-endo-trimethylenenorbornene-2 synthesized according to the method of Cristol et al (J. Am. Chem. Soc., 82, 2351 (1960)) and 200 ml of petroleum ether, and 54 g (1 mole) of sodium methylate was added thereto. Then, 153 g (0.8 mole) of ethyl trichloroacetate was added dropwise to the mixture over a period of 4 hours under agitation on an ice-sodium chloride bath so that the temperature of the reactants did not rise above 0°C. After completion of the dropwise addition, the mixture was further agitated at a temperature below 0°C. for 2 hours, and then the temperature was gradually raised to room temperature and the mixture was agitated overnight. The reaction mixture was added to a mixture of 150 g of ice and 100 ml of water, and the water layer that separated was extracted 4 times with 60 ml of diethyl ether. The water layer was neutralized with 10 percent hydrochlorlic acid and was extracted twice with 60 ml of diethyl ether. The extracts were combined with the organic layer, and the mixture was washed with a saturated solution of sodium chloride, dried with anhydrous sodium sulfate and fractionated.

A fraction boiling at 123°–124°C. under 2 mm Hg was collected to obtain 41.9 g (yield = 77 percent) of 3,4-dichloro-6,7-endo-trimethylenebicyclo[3.2.1]oct-2-ene(VII).

$n_D^{22.5}$ : 1.5447

Elemental Analysis: Found: C, 61.1; H, 6.3; Cl, 32.1 Calculated for $C_{11}H_{14}Cl_2$: C, 60.85; H, 6.50, Cl, 32.65 ir (cm$^{-1}$): 2950, 2870, 1628, 1445, 1355, 1055, 960, 773, 718 ms (m/e) (relative intensity, %): 218 (6), 216 (9), 181 (17), 115 (17), 114 (10), 113 (45), 112 (14), 79 (11), 77 (32), 69 (100), 68 (18), 67 (23), 41 (12) $^1$H nmr (CDCl$_3$ solvent,δ): 6.05 (doublet, J = 7.0 Hz, 1H,

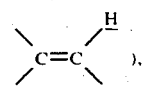

), 4.37 (doublet, J = 1.0 Hz, 1H, >C$\underline{H}$Cl), 3.0 – 1.0 (complex multiplet, 12H)

b. Synthesis of 6,7-endo-trimethylenebicyclo[3.2.1]oct-2-ene (VIII):

300 ml of liquid ammonia was charged in a round-bottom flask of a 1 liter capacity cooled by dry ice-acetone, and 35.4 g (1.54 gram-atoms) of metallic sodium was added thereto over a period of 30 minutes. The mixture was agitated for 30 minutes at a temperature of approximately -50°C. A solution formed by dissolving in 50 ml of dried diethyl ether, 17.35 g (0.08 mole) of 3,4-dichloro-6,7-endo-trimethylenebicyclo[3.2.1]oct-2-ene (VII) prepared by the above method was added dropwise to the mixture over a period of 35 minutes at a temperature of approximately -50°C. The mixture was agitated at this temperature for 30 minutes. The cooling vessel was removed from the reaction system, and 300 ml of diethyl ether was added dropwise to the reaction mixture while distilling off the remaining ammonia. The remaining metallic sodium and sodium amide were carefully decomposed by adding first methanol diluted with diethyl ether, then methanol and finally water. The organic layer was separated, and the water layer was extracted twice with 200 ml of diethyl ether. The ether extracts were combined with the organic layer, and the mixture was washed with a saturated aqueous solution of sodium chloride, dried with anhydrous sodium sulfate and fractionated.

A fraction boiling at 76°C. under 5 mm Hg was recovered to obtain 4.54 g (yield = 38.4 %) of 6,7-endo-trimethylenebicyclo[3.2.1]-oct-2-ene (VIII).

Elemental Analysis Values: Found: C, 88.9; H, 11.1 Calculated for $C_{11}H_{16}$: C, 89.12; H, 10.88 ir (cm$^{-1}$): 3040, 3015, 2920, 2850, 2825, 2670, 1720, 1635, 1465, 1440, 1385, 1285, 1000, 935, 895, 755, 690 ms (m/e) (relative intensity, %): 148 (M$^+$, 27), 94 (16), 91 (15), 81 (11), 80 (40), 79 (100), 78 (72), 77 (12), 67 (14), 66 (11)

$^1$H nmr (CDCl$_3$ solvent, δ): 5.24 – 5.98 (2H, complex multiplet), 1 – 2.92 (14H, complex multiplet)

c. Synthesis of 6,7-endo-trimethylenebicyclo [3.2.1]-octane (I):

An autoclave of 100 ml capacity was charged with 3.1 g (0.021 mole) of 6,7-endo-trimethylenebicyclo[3.2.1]oct-2-ene (VIII) prepared by the above method, 40 ml of diethyl ether and 90 mg of palladium on carbon. Hydrogen was introduced into the autoclave under pressure so that the initial hydrogen pressure was 6 Kg/cm$^2$, and the mixture was agitated at room temperature for 1 hour. The catalyst was removed from the reaction mixture by filtration, and the filtrate was concentrated to obtain 3 g (yield: 95%) of crude 6,7-endo-trimethylenebicyclo[3.2.1]octane (I). The purity of the product was 95 percent as measured on gas chromatography.

Melting Point: 40°– 42°C (sealed tube)

Elemental Analysis: Found: C, 87.8; H, 12.2 Calculated for $C_{11}H_{18}$: C, 87.92; H, 12.08 ir (cm$^{-1}$): 2950, 2900, 2835, 2600, 1460, 1450, 1435, 1320, 1300, 1270, 1230, 1200, 1065, 1040, 960, 890, 870, 850, 770, 720, 660 ms (m/e) (relative intensity, %): 150 (100), 108 (30), 93 (25), 82 (90), 81 (40), 80 (28), 79 (32), 67 (81)

$^1$H nmr (CDCl$_3$ solvent, δ): 2.3 – 2.8 (2H, complex multiplet), 1.1 – 2.2 (16H, complex multiplet)

EXAMPLE 1

A solution of 3.0 g (0.02 mole) of 6,7-endo-trimethylenebicyclo[3.2.1]octane (I) in 50 ml of methylene chloride was agitated at a temperature of 0°C. and 3.0 g (0.02 mole) of trifluoromethanesulfonic acid was added thereto and the mixture was heated and refluxed under agitation for 8 hours.

The reaction mixture was allowed to cool to room temperature and then was added to 50 ml of ice water. The organic layer was separated and the water layer was extracted with methylene chloride. The methylene chloride extract was combined with the organic layer, and the mixture was washed with a saturated aqueous solution of sodium hydrogencarbonate and water, and dried with anhydrous sodium sulfate. Methylene chloride was distilled off and a fraction boiling at 110°–112°C. under 33 mm Hg was collected to obtain 2.4 g (yield = 80%) of tricyclo[5.3.1.0$^{3,8}$]undecane (II).

Melting Point: 62°–63°C (sealed tube)

Elemental Analysis: Found: C, 87.8; H, 12.3 Calculated for C$_{11}$H$_{18}$: C, 87.92, H, 12.08 ir (cm$^{-1}$): 2925, 2890, 2870, 2850, 1480, 1465, 1440, 1340, 975, 940, 895, 845 ms (m/e) (relative intensity, %): 150 (M$^+$, 100), 122 (39), 121 (39), 109 (12), 108 (16), 107 (19), 93 (27), 81 (27), 80 (46), 79 (40), 67 (35), 55 (18), 41 (40)

$^1$H nmr (CDCl$_3$ solvent, δ): 1.0 – 2.0 (complex multiplet)

$^{13}$C nmr (CDCl$_3$ solvent, 15.1 MHz, TMS at 0 ppm) (ppm): 15.2, 24.8, 26.3, 27.1, 30.9, 31.9, 32.3, 33.1

EXAMPLE 2

A solution of 3.0 g (0.02 mole) of 6,7-endo-tricyclo[3.2.1]octane (I) in 50 ml of methylene chloride was agitated at 0°C., and 0.13 g (0.001 mole) of anhydrous aluminum chloride was added to the solution. The mixture was heated and refluxed under agitation for 2 hours. The reaction mixture was allowed to cool to room temperature and then was added to 50 ml of ice water. After the organic layer was separated, the water layer was extracted with methylene chloride and the methylene chloride extract was combined with the organic layer. The mixture was washed with a saturated aqueous solution of sodium hydrogencarbonate and water, and dried with anhydrous sodium sulfate. Methylene chloride was distilled off and the residue was fractionated. A maximum boiling point fraction (boiling at 73° to 75°C. under 5 mm Hg) was collected to obtain 2.2 g (yield: 73%) of tricyclo[5.3.1.0$^{3,8}$]undecane (II). The results of the infrared absorption spectrum analysis, the nmr spectrum analysis and the mass spectrum analysis of the thus-obtained product were in agreement with those of the product (II) obtained in Example 1.

The embodiments of the invention in which an exclusive property or privilege is claimed are defined as follows:

1. A process for preparing tricyclo[5.3.1.0$^{3,8}$]undecane (II) which comprises isomerizing 6,7-endo-trimethylenebicyclo[3.2.1]octane (I), at a temperature in the range of from −30° to +100°C., in the presence of an acid catalyst selected from the group consisting of (1) at least one Bronsted acid, and (2) at least one Lewis acid in an amount of 0.01 to 0.5 mole per mole of I; terminating the isomerization reaction when the content of II in the reaction mixture is at least about 60 weight percent; and recovering II from the reaction mixture.

2. The process according to claim 1 wherein the temperature of the isomerization reaction is in the range of −10° to 50°C.

3. The process according to claim 1 in which the acid catalyst is at least one Bronsted acid selected from the group consisting of sulfuric acid, fluorosulfonic acid, chlorosulfonic acid, methanesulfonic acid, trifluoromethanesulfonic acid, ethanesulfonic acid, benzenesulfonic acid and p-toluenesulfonic acid.

4. The process of claim 1 in which the acid catalyst is at least one Lewis acid selected from the group consisting of boron trifluoride, aluminum halides and antimony halides.

5. The process of claim 1 in which the isomerization reaction is carried out in the presence of an inert solvent.

* * * * *